United States Patent [19]

Silvian

[11] Patent Number: 5,466,246
[45] Date of Patent: Nov. 14, 1995

[54] TELEMETRY RECEIVER FOR IMPLANTABLE DEVICE, INCORPORATING DIGITAL SIGNAL PROCESSING

[75] Inventor: Sergiu Silvian, La Crescenta, Calif.

[73] Assignee: Pacesetter, Inc., Sylmar, Calif.

[21] Appl. No.: 282,997

[22] Filed: Jul. 29, 1994

[51] Int. Cl.⁶ .................................................. A61N 1/362
[52] U.S. Cl. ............................................ 607/32; 128/904
[58] Field of Search ........................ 607/32, 60; 128/904

[56] References Cited

U.S. PATENT DOCUMENTS

| | | | |
|---|---|---|---|
| 4,531,523 | 7/1985 | Anderson | 128/903 |
| 4,571,589 | 2/1986 | Slocum et al. | 607/32 |
| 4,681,111 | 7/1987 | Silvian | 128/903 |
| 4,979,506 | 12/1990 | Silvian | 128/903 |
| 5,085,224 | 2/1992 | Galen et al. | 128/903 |
| 5,117,825 | 6/1992 | Grevious | 607/60 |
| 5,241,961 | 9/1993 | Henry | 607/32 |
| 5,264,843 | 11/1993 | Silvian | 128/903 |

*Primary Examiner*—William E. Kamm
*Attorney, Agent, or Firm*—Lisa P. Weinberg

[57] ABSTRACT

An improved programmer apparatus for receiving digital data telemetered from an implantable device such as a heart pacemaker with substantially reduced hardware complexity and with convenient flexibility to adapt to data received in multiple modulation formats and data rates. The apparatus includes a conventional front-end receiver for receiving the data in both a reflected-impedance telemetry mode and an active telemetry mode, and it further includes a digital signal processor for efficiently processing data samples of the received telemetry data. Processing the received data in software allows for great processing flexibility, including a convenient reconfiguration to accommodate new modulation formats and data rates for implantable devices developed at a later time.

18 Claims, 2 Drawing Sheets

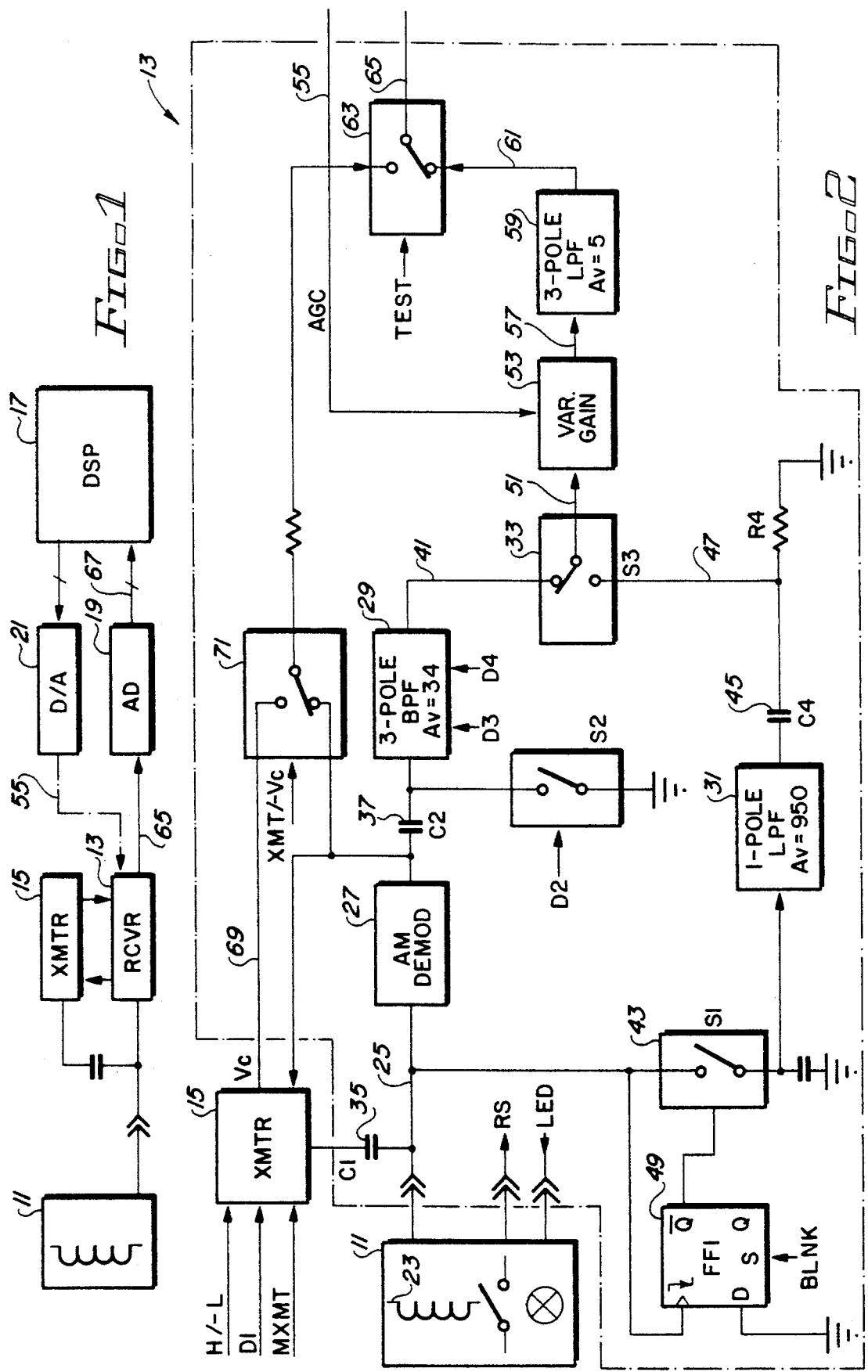

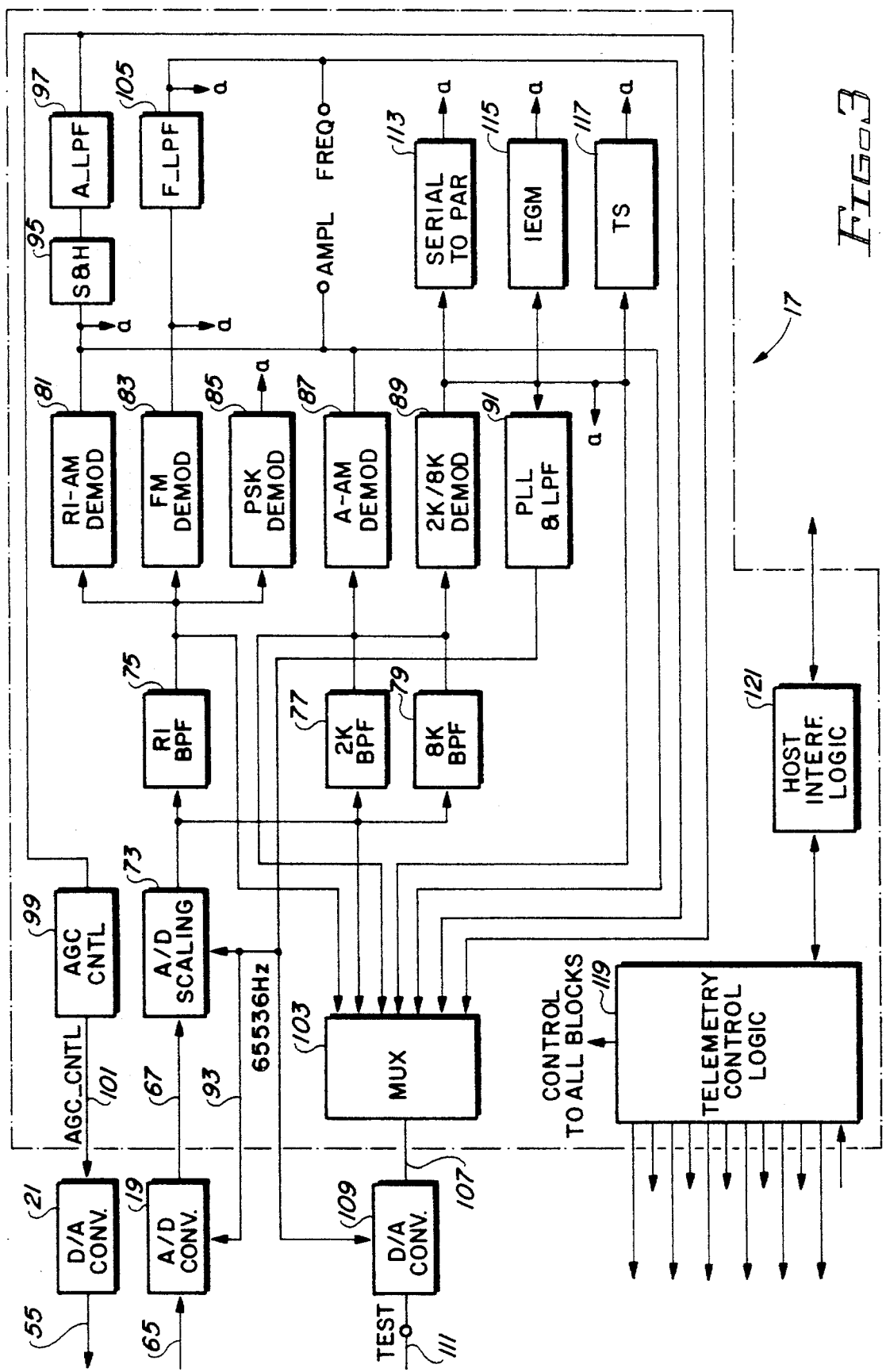

TELEMETRY RECEIVER FOR IMPLANTABLE DEVICE, INCORPORATING DIGITAL SIGNAL PROCESSING

BACKGROUND OF THE INVENTION

This invention relates generally to telemetry receivers for use with implantable devices such as heart pacemakers and, more particularly, to telemetry receivers adapted to process data received from such devices in any of a number of possible modulation formats.

Implantable devices such as heart pacemakers ordinarily accumulate data indicating the condition of various of the pacemaker's internal parameters, as well as a log of pacing activity and of the heart's condition. Periodically, this accumulated data is transmitted via telemetry to an external device, called a programmer. The transmitted data is modulated according to any of a number of conventional modulation schemes, including amplitude modulation, frequency modulation and phase modulation. The transmitted data also is received in any of a number of conventional data rates and frequencies.

Typical programmers have in the past included various bandpass filters and demodulators for demodulating and detecting the telemetered data signal. Appropriate switches are provided for directing the received data signal to the appropriate hardware circuits according to the signal's known format.

Data signals commonly are telemetered by the implantable device in either of two conventional modes, including a reflected-impedance mode and an active mode. In the reflected-impedance mode, the implantable device merely opens and closes a switch connected across a coil, in accordance with the data to be transmitted. Internal power is not utilized to generate electromagnetic radiation; instead, the device provides a variable load on electromagnetic radiation transmitted by the programmer, which is detected by the programmer. In the active telemetry mode, on the other hand, the implantable device utilizes internal electrical power to transmit the data outwardly via an antenna. Many programmers include front-end receiver hardware adapted to receive data telemetered via both the reflected-impedance mode and the active mode.

The programmers described briefly above have proven to be effective in receiving data telemetered from implantable devices and modulated according to any of a number of conventional schemes and data rates. Although such programmers have performed generally effectively, they are considered to be unduly complex and bulky. There is a need for a programmer apparatus of this kind that is configurable to receive and demodulate data telemetered from a variety of implantable devices according to many different modulation schemes, with reduced complexity and size. The present invention fulfills this need.

SUMMARY OF THE INVENTION

The present invention is embodied in an apparatus for receiving a data signal telemetered from an implantable device and modulated by digital data according to any of a number of distinct modulation modes. The apparatus includes a front-end receiver for receiving and amplifying the modulated data signal and an analog-to-digital converter for sampling the amplified signal to produce a sequence of digitized samples. In addition, a digital signal processor is included for implementing a plurality of bandpass filters and plurality of demodulators, including an amplitude demodulator, a frequency demodulator, and a phase demodulator. Further, the digital signal processor filters the sequence of digitized samples using a selected one of the plurality of bandpass filters and then demodulates the filtered sequence of samples using a selected one of the plurality of demodulators. A demodulated signal thereby is produced without the need for unnecessarily duplicative hardware filters and demodulators.

In a more detailed feature of the invention, the front-end receiver includes an antenna for receiving the modulated data signal via electromagnetic radiation, either in a reflected-impedance telemetry mode or in an active telemetry mode. A separate channel of the receiver is configured to amplify the signal received in each telemetry mode. The apparatus further can include a transmitter for transmitting a data signal via the antenna to the implantable device.

In another feature of the invention, the digital signal processor can include a phase-locked loop for synchronizing a phase signal with the phase of the demodulated signal. This phase signal is applied to the analog-to-digital converter, to controllably adjust the timing of its sampling of the amplified modulated data signal. The digital signal processor further can include means, associated with the amplitude demodulator, for producing a feedback signal proportional to the average amplitude of the demodulated signal. This feedback signal is applied to a variable-gain amplifier that is part of the receiver to controllably adjust the amplitude of the modulated data signal.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a simplified block diagram of a programmer apparatus for receiving and transmitting a telemetered data signal from an implantable device, the apparatus incorporating a digital signal processor for filtering and demodulating the received data signal.

FIG. 2 is a more detailed block diagram of the front-end receiver and transmitter portions of the programmer apparatus of FIG. 1.

FIG. 3 is a more detailed block diagram of the digital signal processor of FIG. 1, showing the hardware-equivalent functions it implements.

DESCRIPTION OF THE PREFERRED EMBODIMENT

With reference now to the illustrative drawings, and particularly to FIG. 1, there is shown a programmer apparatus for transmitting and receiving digital data to and from an implantable device such as a heart pacemaker (not shown). The apparatus includes a telemetry wand 11 for receiving a modulated data signal from the implantable device, along with a front-end receiver 13 for filtering and amplifying the received signal. A transmitter 15 also is connected to the wand, for selectively transmitting programming data and instructions to the implantable device and for cooperating with the receiver in receiving the data signal in one telemetry mode.

The programmer apparatus is adapted for use with multiple types of implantable devices, which transmit data using different modes of telemetry and using different forms of modulation, different frequencies, and different data rates. The apparatus filters and demodulates the received telemetered signal to produce a baseband data signal constituting the received data.

The filtering and demodulating function is conveniently and efficiently accomplished in software, using a digital signal processor (DSP) 17, which receives the amplified signal from the front-end receiver 13 via an analog-to-digital (A/D) converter 19. The digital signal processor implements several different bandpass filters and several different demodulators, including an amplitude demodulator, a frequency-shift keyed (FSK) demodulator, and a phase-shift keyed (PSK) demodulator. The digital signal processor automatically selects the particular bandpass filter and demodulator to process the digitized signal. A properly demodulated data signal thereby is produced, regardless of the modulation scheme and data rate utilized by the implantable device.

An additional function implemented by the digital signal processor 17 is the control of a variable-gain amplifier included in the receiver 13. This ensures that the front-end receiver supplies to the A/D converter an amplified data signal having a desired peak amplitude. To facilitate the automatic gain control, the programmer apparatus further includes a digital-to-analog (D/A) converter 21, which converts a digital control word supplied from the digital signal processor to a corresponding analog level for controlling the variable-gain amplifier.

With reference now to FIG. 2, there is shown a more detailed block diagram of the front-end receiver 13 and the transmitter 15 of the programmer apparatus of FIG. 1. The front-end receiver is configured to receive and amplify the modulated data signal received in either of two telemetry modes, including a reflected-impedance mode and an active mode. In both cases, the modulated data signal is received by a pick-up coil 23 of the telemetry wand 11. The coil delivers the received signal on line 25 to two separate channels. An upper channel includes the transmitter 15, an amplitude demodulator 27, and a bandpass antialias filter 29 for receiving modulated data signals transmitted in the reflected-impedance telemetry mode. A lower channel includes a low-pass antialias filter 31 for receiving modulated data signals transmitted in the active telemetry mode. A selection between the two channels is made using a switch 33, which receives the analog output signals from the bandpass filter 29 and the low-pass filter 31.

More particularly, when the programmer apparatus has been configured for receiving a modulated data signal transmitted in a reflected-impedance telemetry mode, the transmitter 15 is caused to couple a predetermined alternating current (AC) signal through a tuning capacitor 35 and along line 25 to the coil 23 of the telemetry wand 11. The AC signal thereby is transmitted from the telemetry wand toward the implantable device. The signal's frequency advantageously can be about 36 kilohertz (KHz). Furthermore, the AC carrier is 100% amplitude modulated for producing either a 100% signal or no signal. When the wand is placed in proximity to the implantable device, the implantable device receiver demodulates the data. To receive data from the implantable device, the transmitter is left ON continuously (no amplitude modulation). The implantable device will, however, impose a small amplitude modulation due to "reflected impedance" and this modulation will be demodulated by the amplitude demodulator 27.

The demodulated signal from the amplitude demodulator 27 is coupled through a coupling capacitor 37 to the bandpass filter 29 to remove noise and frequencies high enough to alias around the digital signal processor sampling frequency of 65536 Hz and to amplify the data signal to a level suitable for further processing. The bandpass filter advantageously can be a simple three-pole filter and can include substantial amplification. The demodulated signal also can be coupled, on line 39, back to the transmitter 15 to provide feedback for controlling its output level while receiving. Reflected-impedance telemetry is described more fully in U.S. Pat. No. 5,264,843, entitled "HIGH SPEED REFLECTED IMPEDANCE TELEMETRY SYSTEM FOR IMPLANTABLE MEDICAL DEVICE," and issued Nov. 23, 1993, in the name of Sergiu Silvian, which is incorporated by reference.

It should be appreciated that, although the 36 KHz carrier frequency of the modulated data signal has been removed by the amplitude demodulator 27, the demodulated signal itself carries the information as a second modulation. This latter modulation can take the form of amplitude modulation, frequency modulation, or phase modulation, depending on the particular implantable device in use. The filtered and amplified modulated data signal is transmitted on line 41 from the bandpass filter 29 to the selector switch 33.

It will be appreciated that the transmitter 15 and wand 11 also can be utilized for transmitting data of various kinds to the implantable device. The transmitter may be appropriately enabled to transmit data either to a reflected-impedance mode type device or to an active mode type device.

When the programmer apparatus has been configured for receiving a modulated data signal transmitted in an active telemetry mode, on the other hand, the transmitter 15 of the upper channel is disabled, and the signal received by the telemetry wand 11 is coupled through a switch 43 to the low-pass filter 31. In the preferred embodiment, this filter is merely a one-pole filter and it provides antialias filtering and a substantial gain to amplify the received signal to a level suitable for further processing. The amplified signal is transmitted through a coupling capacitor 45 and along line 47 to the selector switch 33.

The selector switch 43 is controlled by a flip/flop 49 such that it is held open whenever the transmitter 15 is switched ON. This removes an undesired load from the transmitter. When the transmitter is switched OFF, as when a modulated data signal is being received in the active mode, the flip/flop automatically will close the switch.

The selector switch 33 selects either the filtered reflected-impedance mode signal present on line 41 or the filtered active mode signal present on line 47, and it couples the selected signal on line 51 to a variable-gain amplifier 53. The gain of this amplifier is controlled by the control signal transmitted on line 55 from the D/A converter 21 (FIG. 1). As previously mentioned, this control signal is selected so as to provide a desired peak amplitude for the amplified signal.

From the variable-gain amplifier 53 the amplified signal is transmitted on line 57 to a three-pole antialias low-pass filter and amplifier 59, for further noise removal and amplification, and in turn on line 61 to a switch 63, which in normal operation provides the receiver output signal on line 65. The A/D converter 19 then samples and digitizes this signal and couples a corresponding sequence of data words on lines 67 to the digital signal processor 17. The gains of the various amplifiers are selected such that the data signal supplied to the A/D converter generally spans the range of 0 to 5 volts. This provides optimum quantization.

As mentioned immediately above, the switch 63 normally transmits filtered data from the low-pass filter 59 to the A/D converter 19. In some circumstances, however, it is desired to monitor one of two signals present in the transmitter 15. The digital signal processor 17 therefore selectively outputs a test control signal, to drive the switch 63 to its upper position. This couples to the A/D converter either the transmitter level signal present on line 39 or a control voltage signal present on line 69. The selection between these two signals is made by a switch 71 under the control of a XMT/–VC control signal supplied by the digital signal processor. The transmitter level signal is proportional to the amplitude of the transmitter signal present on line 25, and the control voltage signal corresponds to an analog command signal present within the transmitter.

The digital signal processor 17 is configured to include the proper filters and demodulators for processing the sequence of data samples that might be received from any of a large variety of conventional implantable devices. The digital signal processor, of course, implements these functions in software, which allows for its great flexibility. For ease of understanding, reference is made to the block diagram of FIG. 3, which depicts these software functions in equivalent hardware blocks.

The sequence of data samples supplied to the digital signal processor 17 on lines 67 are initially scaled in an A/D scaling block 73, which transforms the scale of the samples into a conventional two's-complement format for further processing. The scaled samples are delivered to three separate bandpass filters, each adapted to process data having a different center frequency and data rate. A first bandpass filter 75 is used when the data has been received in the reflected-impedance telemetry mode, while the second bandpass filter 77 and the third bandpass filter 79 are used when the data has been received in the active telemetry mode. The second bandpass filter 77 is configured to have a bandwidth sized to accommodate a data rate of 2 kilobits per second, while the third bandpass filter 79 is configured to have a bandwidth sized to accommodate a data rate of 8 kilobits per second.

Filtered data output by the reflected-impedance bandpass filter 75 is selectively transferred to three separate demodulators, including an amplitude demodulator 81, an FSK demodulator 83, and a PSK demodulator 85. Each demodulator is enabled only when the data being processed is modulated according to the corresponding modulation scheme. Each such demodulator provides a demodulated data signal, for further processing.

The second and third bandpass filters 77 and 79, respectively, which are used when data has been received via the active telemetry mode, deliver their filtered output data samples to both an amplitude demodulator 87 and a 2K/8K demodulator 89 for appropriate demodulation. Likewise, these demodulated output samples are provided as demodulated output signals for further processing.

The data samples output by the 2K/8K demodulator 89 also are applied to a phase-locked loop 91, which provides an appropriate clocking signal on line 93 for controlling the sampling of the modulated data signal effected by the A/D converter 19. This enables the sampling to be properly phased with the modulated data signal. The phase-locked loop function is considered important only when data is being received at the higher, 8 kilobit per second rate; it is not considered necessary when receiving data at the lower, 2 kilobit per second rate. This same clocking signal also is utilized to clock the A/D scaling block 73 within the digital signal processor 17, which of course must be synchronized with the A/D converter.

As previously mentioned, the digital signal processor 17 outputs a control signal for coupling through the D/A converter 21 to the variable-gain amplifier 53 of the receiver 13. This control signal varies according to the peak amplitude of the demodulated amplitude modulated signal. Thus, as shown in FIG. 3, a sample-and-hold circuit 95 and a low-pass filter 97 are provided for producing a signal whose value varies according to peak amplitude. In particular, the sample-and-hold circuit repeatedly samples the demodulated signal output by either the reflected-impedance mode amplitude demodulator 81 or the active mode amplitude demodulator 87 each time a "one" bit is being received. Each sample is held until the next "one" bit is received, and the low-pass filter 97 time-averages the successive samples to provide a good measure of the average peak amplitude. The filter output is coupled through an AGC control block 99 to produce the control signal output on line 101 to the D/A converter 21.

To facilitate a proper testing of the digital signal processor 17 during its development, it is configured to include a multiplexer 103 that provides a digital output signal representing various signals present throughout the digital signal processor. In particular, provided as inputs to the multiplexer are: 1) the A/D scaled data output by the A/D scaling block 73; 2) the data output by the bandpass filter 75; 3) the data output by the 2K bandpass filter 77 and the 8K bandpass filter 79; 4) the data output by the 2K/8K demodulator 89; 5) the data output by either the reflected-impedance mode amplitude demodulator 81 or the active mode amplitude demodulator 87; 6) the AGC level output by the low-pass filter 97; and 7) a low-pass filtered version of the demodulated signal output by the FSK demodulator 83, produced by a low-pass filter 105. The multiplexer 103 selects from these seven data signals and provides the selected signal as an output on line 107. A D/A converter 109, under the clocking control of the phase-locked loop 91, converts these sequential data samples into a corresponding analog signal. The analog signal is provided as a test point 111.

The digital signal processor 17 also is configured to include a serial-to-parallel block 113, an intracardiac electrogram (IEGM) block 115, and a test signal 117, all receiving as an input the demodulated data from the 2K/8K demodulator 89. The serial-to-parallel block 113 simply reformats the demodulated data into an 8-bit parallel format. The IEGM block 115 transforms the data into a standard intracardiac electrogram format, and it is enabled only when the demodulated data is of the appropriate kind. The test signal block 117 provides a signal when the data samples supplied to the digital signal processor represent test signals such as those associated with the transmitter 15 (FIG. 2), selected by the test switches 63 and 71.

Included in the digital signal processor 17 is a telemetry control logic block 119, which appropriately configures the digital signal processor so as to properly process the incoming data samples. The telemetry control logic block also outputs appropriate control signals for configuring the transmitter 15, the various switches 33, 43, 63 and 71, and the bandpass filter 29 included in the receiver 13 (FIG. 2). In particular, the telemetry control logic block configures the receiver and digital signal processor in a sequential, trial-and-error mode. It sequentially configures the circuits for each of a plurality of known implantable device protocols, is properly demodulated. Such digital signal processor control is well within the abilities of those skilled in the relevant art.

The digital signal processor 17 interfaces with additional circuitry (not shown) via a host interface logic block 121.

Those skilled in the art will appreciate the conventional nature of outputting demodulated data in desired formats and of receiving data instructions and data for transmission.

It should be appreciated from the foregoing description that the present invention provides an improved programmer apparatus for receiving telemetry data from an implantable device such as a heart pacemaker, with substantially reduced hardware complexity and with convenient flexibility to adapt to data received in multiple modulation formats and data rates. The apparatus includes a conventional receiver for receiving the data in both a reflected-impedance telemetry mode and an active telemetry mode, and it further includes a digital signal processor for efficiently processing data samples of the received telemetry data. Processing the received data in software allows for great processing flexibility, including a convenient reconfiguration to accommodate new modulation formats and data rates for implantable devices developed at a later time.

Although the invention has been described in detail with reference only to the presently preferred embodiment, those of ordinary skill in the art will appreciate that various modifications can be made without departing from the invention. Accordingly, the invention is defined only by the following claims.

What is claimed is:

1. Apparatus for receiving a modulated data signal transmitted from an implantable device, wherein the modulated data signal is modulated by a digital or an analog data signal in any of a plurality of distinct modulation modes, the apparatus comprising:

front-end receiving means for receiving the modulated data signal from the implantable device, the front-end receiving means including means for amplifying and antialias filtering the received signal;

analog-to-digital converter means for sampling the amplified modulated data signal to produce a sequence of digitized samples; and digital signal processing means for filtering the sequence of digitized samples using at least one of a plurality of bandpass filters and for demodulating the filtered sequence of digitized samples using at least one of a plurality of demodulators, including an amplitude demodulator, a frequency demodulator, and a phase demodulator, to produce a demodulated data signal.

2. Apparatus, as defined in claim 1, wherein:

the front-end receiving means includes a variable-gain amplifier having a gain which can be variably adjusted;

the digital signal processing means includes means, associated with the amplitude demodulator, for producing a feedback signal proportional to the average amplitude of the demodulated signal and for providing the feedback signal to the variable-gain amplifier to controllably adjust the gain until a desired peak amplitude of the amplified modulated data signal is obtained.

3. Apparatus, as defined in claim 1, wherein:

the front-end receiving means includes an antenna for receiving the modulated data signal from the implantable device, the signal being an electromagnetically radiated signal which has been transmitted from the implantable device by one of a reflected-impedance transmission mode or an active transmission mode;

the means for amplifying and antialias filtering the received signal includes:

first channel means for AM demodulating, amplifying, and filtering the received modulated data signal when it has been received by the reflected-impedance transmission mode;

second channel means for amplifying and filtering the received modulated data signal when it has been received by the active transmission mode; and switching means for selecting the first channel when the modulated data signal has been received by the reflected-impedance transmission mode and for selecting the second channel when the modulated data signal has been received by the active transmission mode.

4. Apparatus, as defined in claim 1, wherein:

the front-end receiving means includes an antenna for receiving the modulated data signal from the implantable device, the signal being an electromagnetically radiated signal, the front-end receiving means further including a demodulator; and the apparatus further includes transmitting means for providing an unmodulated, continuous carrier signal to the implantable device, the carrier signal being amplitude modulated by a data signal from the implantable device during a reflected-impedance transmission mode to produce a reflected-impedance modulated data signal;

whereby the front-end receiving means removes the carrier frequency by demodulating the reflected-impedance modulated data signal.

5. Apparatus, as defined in claim 4, wherein:

the transmitting means includes means for selectively transmitting programming data and instructions to the implantable device in either a reflected-impedance modulation mode or in an active transmission modulation mode.

6. Apparatus, as defined in claim 1, wherein:

the digital signal processing means includes means for synchronizing sampling by the analog-to-digital converter means with the amplified modulated data signal.

7. Apparatus, as defined in claim 1, wherein the digital signal processing means includes means for selecting from the plurality of bandpass filters and from the plurality of demodulators in a sequential fashion until it is determined that the modulated data signal has been properly demodulated.

8. A telemetry system for an implantable device, comprising:

front-end receiving means for receiving a modulated data signal from the implantable device, the modulated data signal being modulated by one of a digital or an analog data signal in one of a plurality of distinct modulation modes, the receiving means including filtering means for amplifying and antialias filtering the received signal;

analog-to-digital converter means for sampling the filtered modulated data signal to produce a sequence of digitized samples; and digital signal processing means for producing a demodulated data signal independent of the modulation mode used, the digital signal processing means including means for filtering the sequence of digitized samples using a plurality of filters and means for demodulating the filtered sequence of digitized samples using a plurality of demodulators; and means for selecting from the plurality of bandpass filters and for selecting from the plurality of demodulators in a sequential fashion until the modulated data signal has been demodulated.

9. The telemetry system, as defined in claim 8, wherein:

the plurality of distinct modulation modes includes a reflected-impedance modulation mode.

10. The telemetry system, as defined in claim 9, wherein:

the reflected-impedance modulation mode includes an amplitude modulation (AM) mode; and the plurality of demodulators includes a reflected-impedance AM demodulator.

11. The telemetry system, as defined in claim 9, wherein:

the reflected-impedance modulation mode includes an frequency modulation (FM) mode; and the plurality of demodulators includes a reflected-impedance FM demodulator.

12. The telemetry system, as defined in claim 9, wherein:

the reflected-impedance modulation mode includes an phase-shift keyed modulation (PSK) mode; and the plurality of demodulators includes a reflected-impedance PSK demodulator.

13. The telemetry system, as defined in claim 8, wherein:

the plurality of distinct modulation modes includes an active transmission modulation mode.

14. The telemetry system, as defined in claim 13, wherein:

the active transmission modulation mode includes an amplitude modulation (AM) mode; and the plurality of demodulators includes an active transmission AM demodulator.

15. The telemetry system, as defined in claim 13, wherein:

the active transmission modulation mode includes a 2K bits per second modulation rate; and the plurality of demodulators includes an active transmission 2K demodulator.

16. The telemetry system, as defined in claim 13, wherein:

the active transmission modulation mode includes a 8K bits per second modulation rate;

the plurality of demodulators includes an active transmission 8K demodulator; and the digital signal processing means includes means for providing a clocking signal for synchronizing the analog-to-digital converter means to sample the amplified modulated data signal according to the clocking signal, so that the analog-to-digital converter is synchronized with the modulated data signal.

17. The telemetry system, as defined in claim 8, further comprising:

transmitting means for selectively transmitting programming data and instructions to the implantable device in either a reflected-impedance modulation mode or in an active transmission modulation mode.

18. The telemetry system, as defined in claim 17, wherein:

the front-end receiving means includes a demodulator; and the transmitting means includes means for providing an unmodulated, continuous carrier signal to the implantable device, the carrier signal being amplitude modulated by a data signal from the implantable device during a reflected-impedance transmission mode to produce a reflected-impedance modulated data signal;

whereby the front-end receiving means removes the carrier frequency by demodulating the received reflected-impedance modulated data signal.

\* \* \* \* \*